(12) United States Patent
Hager et al.

(10) Patent No.: US 8,764,710 B2
(45) Date of Patent: Jul. 1, 2014

(54) BLOOD EXPOSURE PREVENTION IN VASCULAR ACCESS DEVICES

(75) Inventors: Jörgen Bruno Hager, Helsingborg (SE); Anders Bengt Erik Nilsson, Helsingborg (SE); Kristoffer Glowacki, Staffanstorp (SE); Karl Johan Mårten Söderholm, Helsingborg (SE); Johan Fredrik Thörne, Helsingborg (SE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 119 days.

(21) Appl. No.: 11/693,285

(22) Filed: Mar. 29, 2007

(65) Prior Publication Data

US 2008/0243086 A1    Oct. 2, 2008

(51) Int. Cl.
*A61M 5/178*    (2006.01)

(52) U.S. Cl.
USPC .............................. 604/164.08; 604/168.01

(58) Field of Classification Search
USPC .............. 604/164.08, 900, 110, 6.07, 168.01
See application file for complete search history.

(56) References Cited

U.S. PATENT DOCUMENTS

| | | | |
|---|---|---|---|
| 3,802,433 A | 4/1974 | Raven | |
| 4,231,367 A | 11/1980 | Rash | |
| 4,728,321 A | 3/1988 | Chen | |
| 4,966,586 A | 10/1990 | Vaillancourt | |
| 5,030,205 A | 7/1991 | Holdaway et al. | |
| 5,092,845 A | 3/1992 | Chang | |
| 5,156,792 A | 10/1992 | Holdaway et al. | |
| 5,246,427 A | 9/1993 | Sturman et al. | |
| 5,419,766 A * | 5/1995 | Chang et al. | 604/110 |
| 5,630,803 A | 5/1997 | Tamaro | |
| 5,810,784 A | 9/1998 | Tamaro | |
| 5,833,670 A | 11/1998 | Dillon et al. | |
| 5,860,937 A * | 1/1999 | Cohen | 600/576 |
| 5,957,892 A | 9/1999 | Thorne | |
| 6,015,397 A | 1/2000 | Elson et al. | |
| 6,117,108 A * | 9/2000 | Woehr et al. | 604/110 |

(Continued)

FOREIGN PATENT DOCUMENTS

| | | |
|---|---|---|
| EP | 1 568 393 A1 | 8/2005 |
| EP | 1 764 123 A1 | 3/2007 |
| WO | WO 92/18182 | 10/1992 |

*Primary Examiner* — Kevin C Sirmons
*Assistant Examiner* — Deanna K Hall
(74) *Attorney, Agent, or Firm* — Jeanne Lukasavage; Craig Metcalf; Kirton McConkie

(57) ABSTRACT

An apparatus for preventing blood exposure or contamination upon withdrawal of a hypodermic needle is provided. The apparatus may include a needle having a tip and a shield configured to at least partially entrap the needle tip upon withdrawal of the needle. The apparatus may further include a blood stabilizing material disposed such that upon withdrawal of the needle the blood stabilizing material is disposed in operative association with the needle tip such that blood carried by the needle is prevented from escaping the apparatus. In some exemplary implementations, the blood stabilizing material may be disposed on one or more surfaces of the shield. The shield of the hypodermic needle may include protective device and/or a housing for shielding the needle tip upon withdrawal. The housing may be adapted to at least partially cover the needle tip upon withdrawal of the needle. In some implementations, the housing may be adapted to allow the protective device to shield the needle before the needle is completely withdrawn.

20 Claims, 9 Drawing Sheets

(56) References Cited

U.S. PATENT DOCUMENTS

| | | |
|---|---|---|
| 6,527,747 B2 | 3/2003 | Adams et al. |
| 6,814,725 B2 | 11/2004 | Gutierrez |
| 7,192,433 B2 | 3/2007 | Osypka et al. |
| 7,238,169 B2 * | 7/2007 | Takagi et al. ............ 604/110 |
| 2006/0036219 A1 | 2/2006 | Alvin |

* cited by examiner

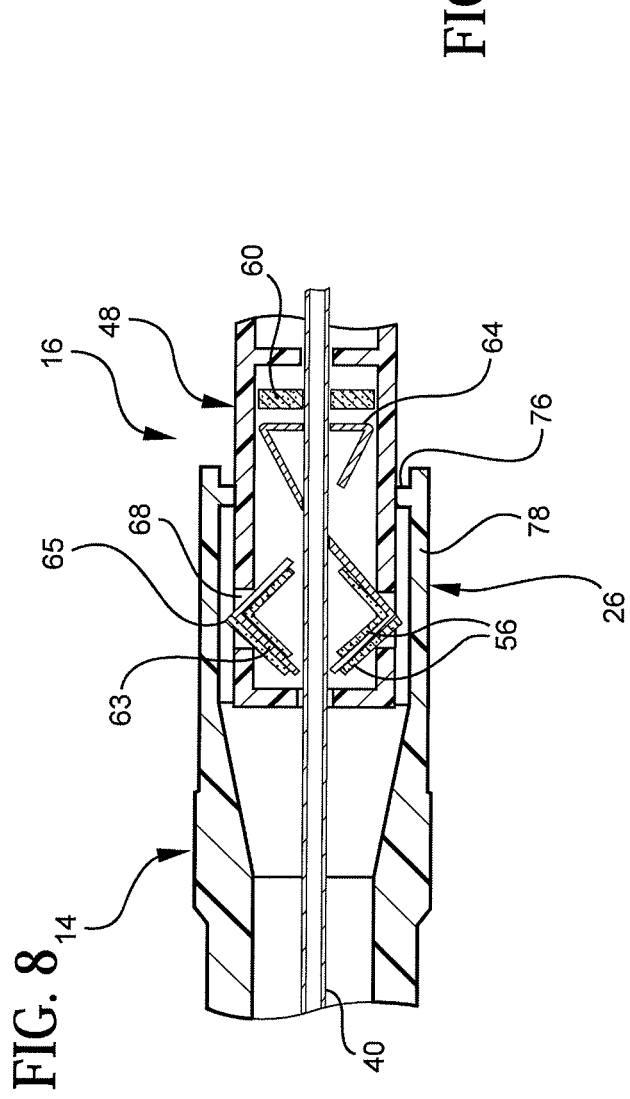
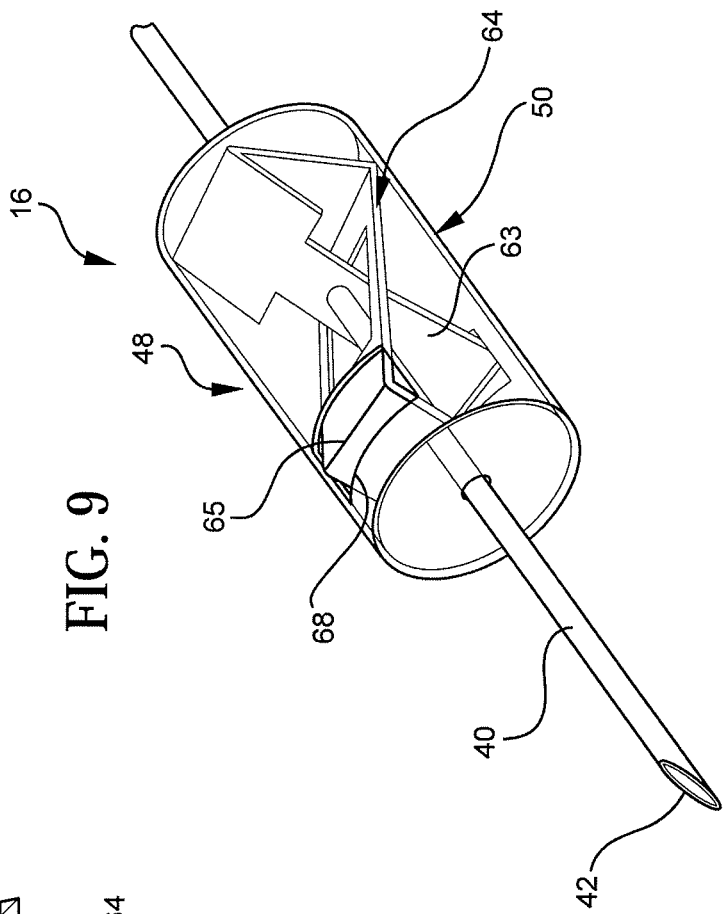
FIG. 8
FIG. 9

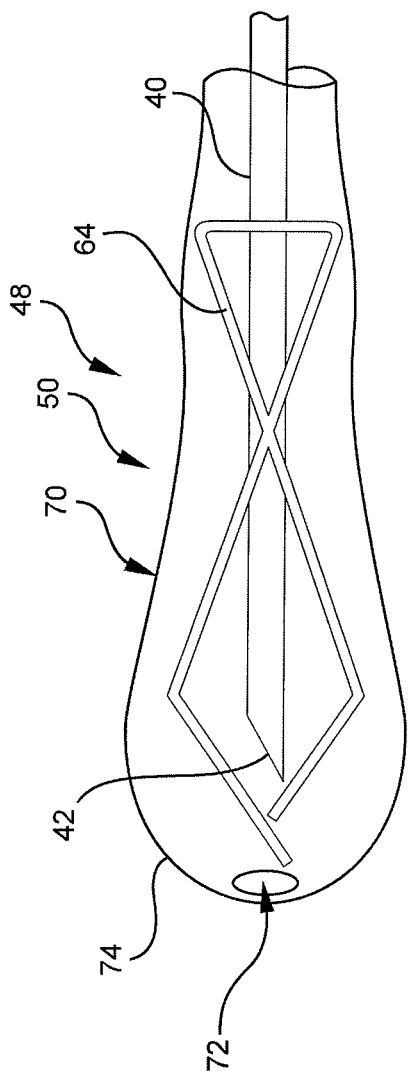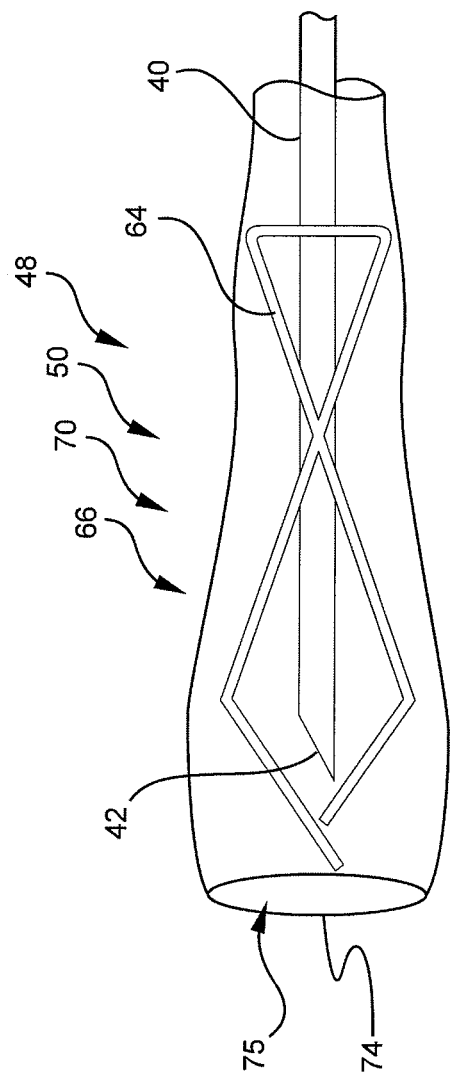
FIG. 11
FIG. 12

BLOOD EXPOSURE PREVENTION IN VASCULAR ACCESS DEVICES

BACKGROUND

This disclosure relates generally to vascular access devices and methods, including hypodermic needles, catheter assemblies, and devices used with catheter assemblies. Generally, vascular access devices are used for communicating fluid with the vascular system of patients. For example, catheters are used for infusing fluid, such as saline solution, various medicaments, and/or total parenteral nutrition, into a patient, withdrawing blood from a patient, and/or monitoring various parameters of the patient's vascular system.

Intravenous (IV) catheter assemblies are among the various types of vascular access devices and over-the-needle peripheral IV catheters are a common IV catheter configuration. As its name implies, an over-the-needle catheter is mounted over an introducer needle having a sharp distal tip. The introducer needle is generally a hypodermic needle coupled to a needle assembly to help guide the needle and to facilitate its cooperation with the catheter. At least the inner surface of the distal portion of the catheter tightly engages the outer surface of the needle to prevent peelback of the catheter and thus facilitate insertion of the catheter into the blood vessel. The catheter and the introducer needle are assembled so that the distal tip of the introducer needle extends beyond the distal tip of the catheter with the bevel of the needle facing up away from the patient's skin. The catheter and introducer needle are generally inserted at a shallow angle through the patient's skin into a blood vessel.

In order to verify proper placement of the needle and/or catheter in the blood vessel, the clinician generally confirms that there is "flashback" of blood in a flashback chamber, which is generally associated with a needle assembly. Once proper placement of the distal tip of the catheter into the blood vessel is confirmed, the clinician may apply pressure to the blood vessel by pressing down on the patient's skin over the blood vessel distal of the introducer needle and the catheter. This finger pressure occludes the vessel, minimizing further blood flow through the introducer needle and the catheter.

The clinician may then withdraw the introducer needle from the catheter. The introducer needle may be withdrawn into a needle tip shield or needle shield that covers the needle tip and prevents accidental needle sticks. In general, a needle tip shield includes a housing, a sleeve, or other similar device that is designed such that when the needle is withdrawn from the patient, the needle tip will be trapped/captured within the needle tip shield. The purpose of the needle tip shield is to house the tip of the needle in a secure location, thereby reducing the possibility of needle sticks when the needle and needle tip shield are separated properly from the catheter, which is left in place to provide intravenous access to the patient.

The separation of the needle assembly from the catheter portions of the catheter assembly presents numerous potential hazards to the clinicians and others in the area. As indicated above, there is a risk of accidental needle sticks if the needle tip is not secured properly in a needle tip shield. Additionally, because the needle has been in contact with blood in the patient's vasculature, blood is often present on the exterior of the needle and is often present inside the lumen of the needle. As the needle is withdrawn, there is a risk that this blood will drip from the needle tip or come into contact with other surfaces to expose clinicians and equipment to blood. Additionally, it has been observed that withdrawing a needle from a catheter assembly often imparts energy to the needle assembly, such as by the intentional or unintentional bending forces applied to the needle during removal. This energy has been observed to cause blood to splatter or spray from the needle as the needle wiggles and shakes with the stored energy once it is free from the catheter assembly. While prior needle assemblies have provided needle tip shields to reduce the occurrence of needle sticks, these prior enclosures and clips have not sufficiently addressed the risk that clinicians and equipment may be exposed to blood from the needle without experiencing a needle stick. While the problem of blood exposure from needle tips used in over-the-needle catheters is a common problem, blood exposure risks are also problematic in other uses of hypodermic needles where the needle tip has been in contact with blood. The present disclosure presents systems and methods to significantly limit and/or prevent such blood exposure.

BRIEF SUMMARY

The systems and methods of the present disclosure have been developed in response to problems and needs in the art that have not yet been fully resolved by currently available vascular access systems and methods. Thus, these systems and methods are developed to provide safer vascular access systems, methods of manufacturing the same, and methods of using the same to reduce blood exposure.

In some aspects of the present disclosure, an apparatus for preventing blood exposure or contamination upon withdrawal of a hypodermic needle is provided. The apparatus may include a needle having a tip and a shield configured to at least partially entrap the needle tip upon withdrawal of the needle. The apparatus may further include a blood stabilizing material disposed such that upon withdrawal of the needle the blood stabilizing material is disposed in operative association with the needle tip such that blood carried by the needle is prevented from escaping the apparatus. In some exemplary implementations, the blood stabilizing material may be disposed on one or more surfaces of the shield.

Additionally or alternatively, the shield of the present disclosure may include a housing and/or a protective device. The housing may at least partially cover the needle tip and, when a protective device is included, may at least partially enclose the protective device. The protective device may incorporate one or more features to shield the needle tip to prevent needle sticks. In some implementations, the housing may be adapted to allow the protective device to shield the needle before the needle is completely withdrawn.

The present disclosure is further directed to methods for preventing blood exposure upon withdrawal of a hypodermic needle. In one exemplary implementation of the present methods, the methods may include providing a hypodermic needle and providing a shield for at least partially covering the tip of the hypodermic needle upon withdrawal. Moreover, the exemplary method may include providing a blood stabilizing material associated with the shield for stabilizing blood carried by the hypodermic needle.

As one example of the variations on the present methods that are within the scope of the present disclosure, suitable methods for preventing blood contamination upon withdrawal of a hypodermic needle may include providing a hypodermic needle having a needle tip and an associated protective device for shielding the needle tip upon withdrawal and providing a housing which covers the protective device and the needle tip upon withdrawal of the needle tip. In such implementations, the housing may be adapted to allow the protective device to shield the needle before the needle is completely withdrawn.

These and other features and advantages of the present disclosure may be incorporated into certain embodiments and will become more fully apparent from the following description and appended claims, or may be learned by the practice of the methods and use of the systems as set forth hereinafter. The present disclosure does not require that all the advantageous features and all the advantages described herein be incorporated into every embodiment.

BRIEF DESCRIPTION OF THE SEVERAL VIEWS OF THE DRAWINGS

In order that the manner in which the above-recited and other features and advantages of the disclosure are obtained will be readily understood, a more particular description will be rendered by reference to specific embodiments thereof which are illustrated in the appended drawings. These drawings depict only typical embodiments and are not therefore to be considered to limit the scope of the present disclosure.

FIG. 8 is another cross-sectional view of an exemplary shield before the needle is withdrawn.

FIG. 9 is a perspective view of the shield of FIG. 8.

FIG. 11 is a side view of an exemplary housing.

FIG. 12 is a side view of an exemplary housing.

DETAILED DESCRIPTION

The presently preferred embodiments of the present disclosure will be best understood by reference to the drawings. It will be readily understood that the components of the present disclosure, as generally described and illustrated in the figures herein, could be arranged and designed in a wide variety of different configurations. Thus, the following more detailed description, as represented in the figures, is not intended to limit the scope of the claims, but is merely representative of presently preferred embodiments.

Figure 1:
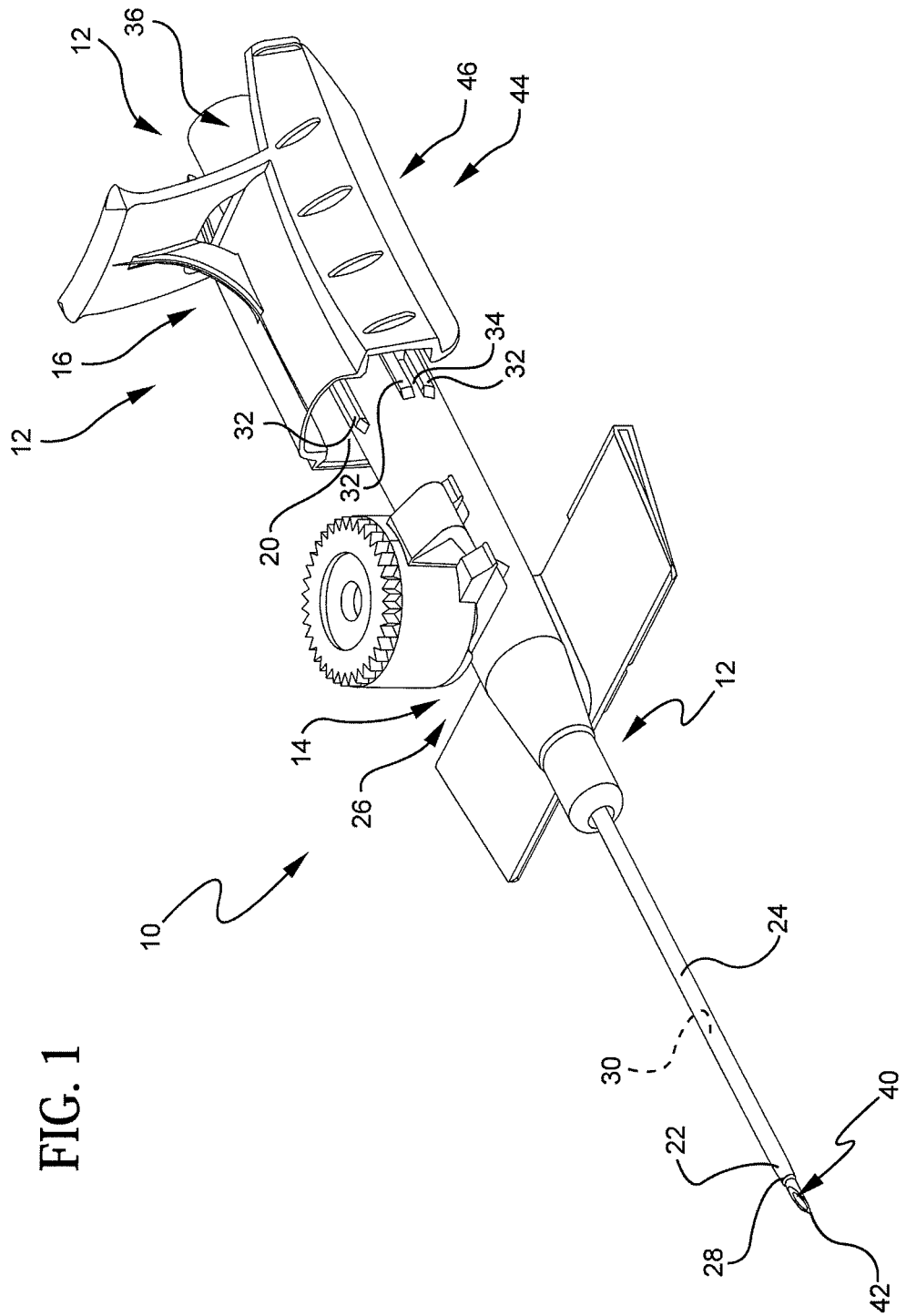
FIG. 1 is a perspective view of an extravascular system.

Referring to FIG. 1, a perspective view illustrates an example of an extravascular system 10 including multiple vascular access devices 12. In this example, the extravascular system 10 includes a catheter assembly 14, and a needle assembly 16. The catheter assembly 14 has a proximal end 20 and a distal end 22 and includes a catheter 24 having an opening 28 at the distal end 22 of the catheter assembly 14 and a catheter hub 26 disposed at the proximal end 20 of the catheter assembly. The catheter assembly 14 also defines a lumen 30 extending from the proximal end 20 to the distal end 22. As illustrated, the catheter hub 26 includes a plurality of positioning ridges 32 and a positioning groove 34. The plurality of positioning ridges 32 and the positioning groove 34 are examples of coupling systems that may be used to position and/or retain another vascular access device, such as adapters, flow control plugs, dead-ender caps, or other devices, attached to the catheter hub 26 in a desired orientation. Other suitable coupling and positioning systems may be used.

Figure 2:
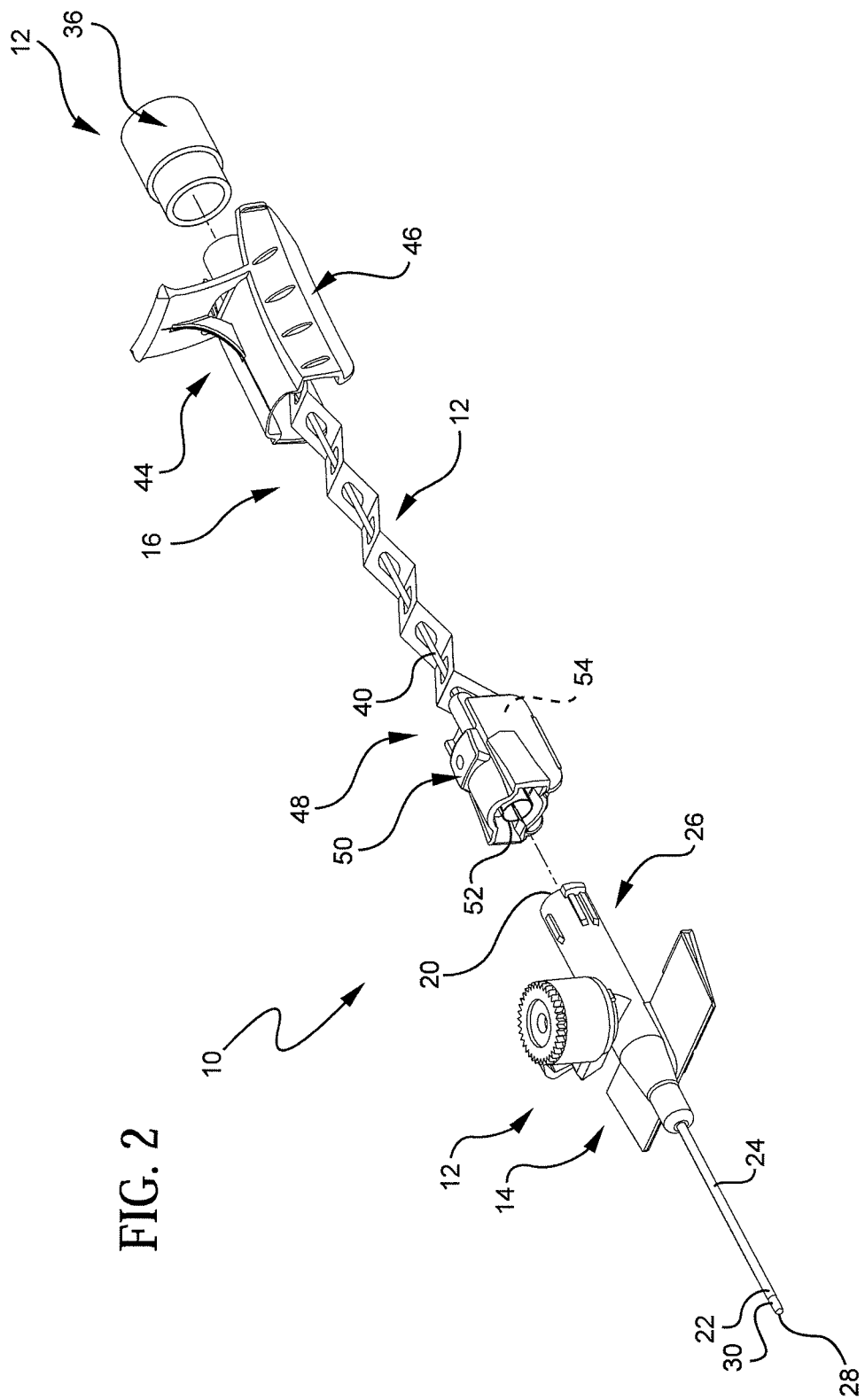
FIG. 2 is an exploded view of the extravascular system of FIG. 1.

The needle assembly 16 includes a hypodermic needle 40 that extends through the lumen 30 of the catheter assembly 14. As illustrated and conventional, the needle tip 42 extends through the opening 28 of the catheter 24. Additionally, the needle assembly 16 may include a variety of features to facilitate the insertion of the extravascular system into a patient's vasculature and the withdrawal of the needle 40 from the catheter assembly 14. For example, the needle assembly 16 may include a needle withdrawal assembly 44, which may include a needle hub 46 and a needle shield 48 (see FIG. 2). FIG. 1 further illustrates that the proximal end of the needle assembly 16 cooperates with yet another vascular access device 12, such as the flow control plug 36. While the needle assembly 16 illustrated in FIGS. 1 and 2 is configured for use with a catheter assembly, other needle assemblies within the scope of the present disclosure may include hypodermic needles adapted for other applications. For example, the needle assembly 16 may or may not include a needle hub 46 of the configuration illustrated. Additional details regarding the needle assembly 16 and subcomponents thereof will be described below.

Referring to FIG. 2, an exploded view of the extravascular system 10 of FIG. 1 shows the needle 40 withdrawn from the catheter 24. As illustrated, the needle tip is drawn into the needle shield 48. The needle shield 48 shown in FIG. 2 is representative of needle shields within the scope of the present disclosure. As used herein, the term needle shield refers to any structure that is adapted to be positioned adjacent the needle tip when the needle tip has been withdrawn, such as withdrawn from a catheter assembly or a patient's vascular system. Examples of conventional needle shields include safety clips of a variety of configurations and housings adapted to encapsulate the needle tip 40 and combinations of the same. While these conventional needle shields have addressed the problems associated with needle sticks by protecting the needle tip, they have failed to provide complete solutions to the risks of blood exposure because the blood is not isolated or secured to avoid splattering, dripping, or otherwise coming into contact with other materials or persons.

Continuing with the discussion of the needle shield 48 illustrated in FIG. 2, it can be seen that the needle shield 48 includes a housing 50, which may provide a full or a partial enclosure 54. As illustrated, the housing 50 includes a passage 52 through which the needle 40 is drawn before entering the enclosure 54 of the housing. The shield 48 may also include one or more protective devices, such as safety clips (not shown), to allow the needle to move freely through the shield 48 as the needle is withdrawn but to prevent the needle tip 42 from advancing distally once it has entered the enclosure. Any of a variety of protective devices may be used in cooperation with the remaining aspects of the present disclosure. While not shown in the high-level perspective view of FIG. 2, the needle shield 48 may also include a blood stabilizing material, which may be disposed on one or more of the surfaces of the needle shield 48, such as on the housing and/or the protective device, or may be associated with one or more aspects of the needle shield. The blood stabilizing material and its use in needle shields 48 is better illustrated in FIGS. 3-9 and discussed in more detail below.

Figure 3:
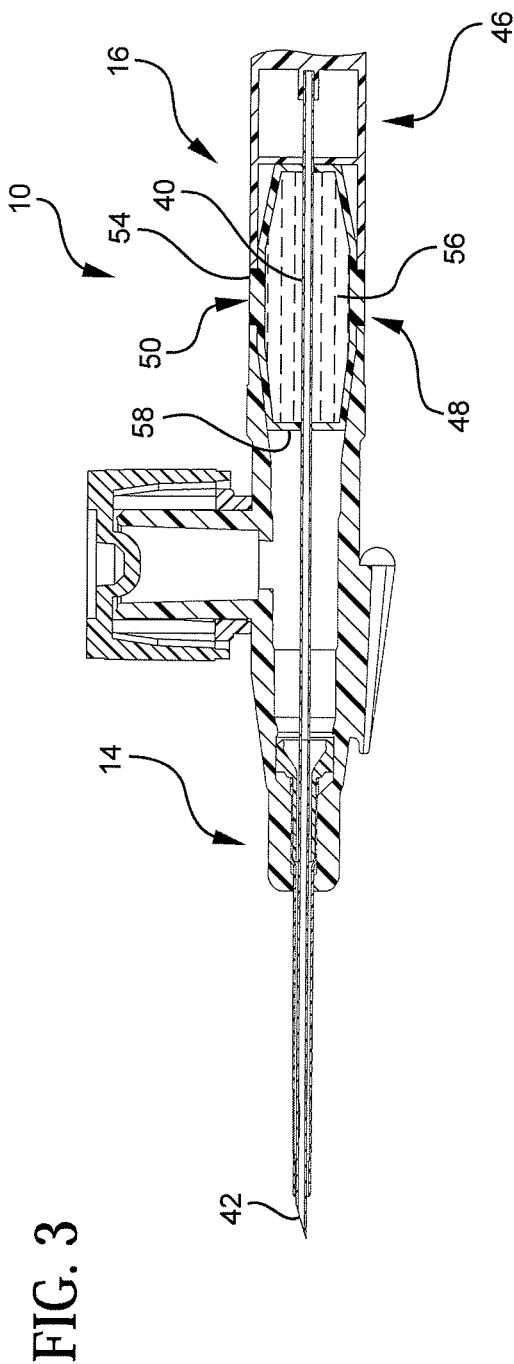
FIG. 3 is a cross-sectional view of an extravascular system incorporating a hypodermic needle.
Figure 4:
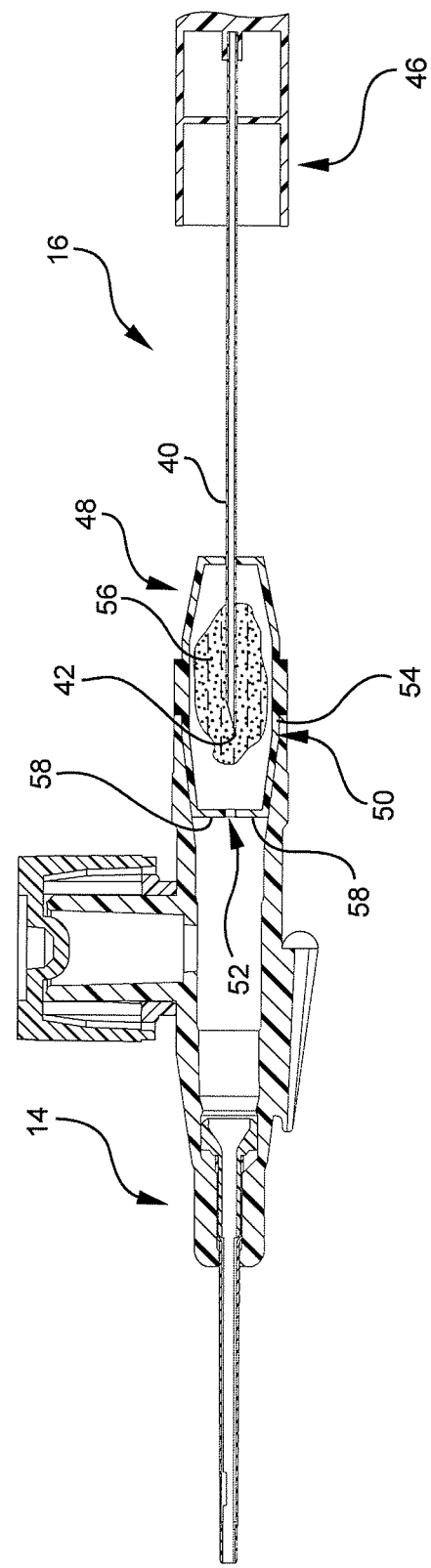
FIG. 4 is an exploded cross-sectional view of the extravascular system of FIG. 3 illustrating the hypodermic needle being separated from another vascular access device.

FIGS. 3 and 4 illustrate a schematic cross-sectional view of an extravascular system 10 including a catheter assembly 14 and a needle assembly 16. Similar to the needle assembly 16 of FIGS. 1 and 2, the needle assembly 16 of FIGS. 3 and 4 includes a needle hub 46 and a needle shield 48. As seen in FIG. 3, the needle shield 48 may be configured to cooperate with the catheter assembly 14 and may slidingly engage the needle 40 to be moved along the length of the needle as it is withdrawn and to be disposed around the needle tip 42 once the needle is withdrawn from the catheter assembly. While schematic, FIGS. 3 and 4 illustrate exemplary implementations of the blood stabilizing material in the needle assembly 16. As illustrated in FIG. 3, the blood stabilizing material 56 is in a liquid form and is maintained within the enclosure 54 by the seals between the housing 50 and the needle 40. Additionally or alternatively, the blood stabilizing material 56 may be provided as a solid material or a gel or colloidal material. As illustrated in FIG. 4, as the needle 40 is withdrawn from the catheter assembly 14 and the blood and fluids on the surface of the needle pass through the enclosure, the blood stabilizing material 56 begins to coagulate or otherwise stabilize the blood within the enclosure. FIG. 4 illustrates that coagulated blood stabilizing material 56 is collected around the needle tip 42 where most of the blood would be present.

In some implementations, the blood stabilizing material 56 may be a coagulant, selected from the current or still to be developed coagulants. Exemplary coagulants may include oxidized regenerated cellulose, microfibrillar collagen, topical thrombin, and fibrin sealants, among others. Additionally or alternatively, the blood stabilizing material 56 may include one or more materials selected to absorb blood, such as micro-porous polysaccharide hemispheres, sodium polyacrylate, purified pork skin gelatin, and carboxy methyl cellulose, among others. Still additionally or alternatively, coagulating and absorbing materials may be used in cooperation to stabilize and immobilize as much blood as possible. Continuing with FIGS. 3 and 4, it can be seen that the blood stabilizing material 56 may be used to stabilize the blood and, when configured to become sufficiently solid, may also function to prevent the needle tip 42 from exiting the enclosure 54.

Continuing with the discussion of FIGS. 3 and 4, the schematic representation of the extravascular device illustrates that the needle shield 48 may be configured to remain coupled to the catheter assembly 14 until the needle tip 42 is drawn into the housing 50, which in this illustration is an enclosure 54, and is in contact with the blood stabilizing material 56. In such implementations, the blood that may be on the outside or inside of the needle 40 may be limited to remaining in the catheter assembly, entering the enclosure, and contacting the distal exterior surfaces 58 of the needle shield 48. Clinicians and others expect the catheter assembly to be contaminated with blood and it presents an expected source of exposure risk. The blood that enters the enclosure 54 is stabilized and immobilized by the blood stabilizing material 56 to thereby minimize and/or eliminate the risk of exposure. Once the blood has been stabilized by absorption and/or coagulation, the risk of blood being splattered is significantly reduced and the exposure risk is still further minimized due to the stability of the blood (i.e., being coagulated or absorbed the blood does not contaminate other objects or persons). The clinician is then left with a single, defined source of blood exposure risk at the distal exterior surface of the needle shield 48.

Figure 6:
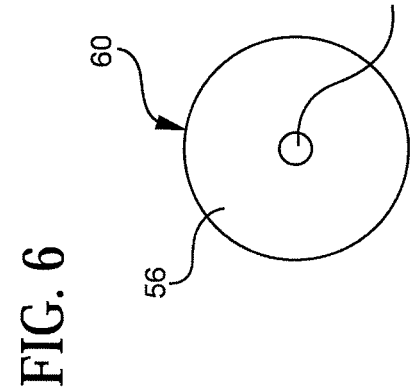
FIG. 6 is a plan view of the exemplary blood stabilizer illustrated in FIG. 5.
Figure 5:
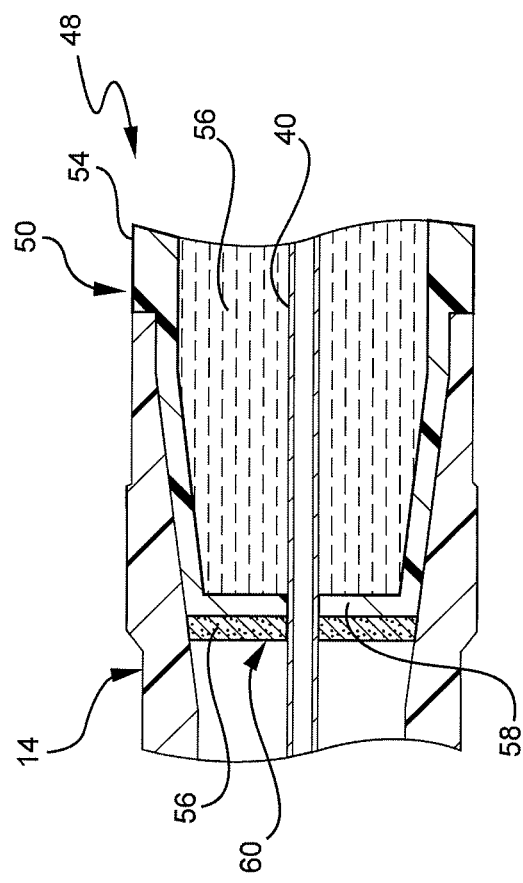
FIG. 5 is a cross-sectional view of a portion a hypodermic needle and associated shield coupled to another vascular access device.

While reducing the exposure risk to the single source at the distal end of the needle shield is an improvement over the conventional needle shields that may have allowed blood to contaminate multiple surfaces, FIGS. 5 and 6 illustrate an additional view of the schematic extravascular assembly 10 showing a blood stabilizing material 56 disposed on the exterior of the needle shield 48. As illustrated, the blood stabilizing material 56 on the exterior of the housing 50 is configured as a solid or semi-solid ring or toroid 60. FIG. 5 presents a side cross-sectional view similar to the views of FIGS. 3 and 4 while FIG. 6 presents a plan view of the ring 60 of blood stabilizing material 56 showing the passage 62 for sliding engagement with the needle. As illustrated in FIGS. 5 and 6, the blood stabilizing material 56 is configured as a separate ring 60 that is coupled or attached to the distal exterior surface 58 of the needle shield 48. However, it should be understood that the blood stabilizing material 56 may be associated with the exterior surfaces of the needle shield 48 in any suitable manner or configuration. For example, the distal exterior surfaces 58 of the needle shield 48 may not be in planar configuration and the blood stabilizing material 56 may be formed to follow the contours of the exterior surfaces 58 rather than as a substantially planar ring. Additionally or alternatively, the blood stabilizing material 56 may be associated with the exterior surfaces as a coating rather than as an attached solid or semi-solid material. For example, a coagulant may be coated on the exterior surfaces of the needle shield 48. Similar to the discussion of FIGS. 3 and 4, the blood stabilizing material 56 used on the exterior of the needle shield 48 may be a coagulant, an absorbent, or another material for stabilizing the blood to reduce the exposure risk. Similarly, the blood stabilizing material 56 may be a liquid, a solid, a gel, or any other consistency appropriate for its use.

While FIGS. 1-5 illustrate needle shields 48 that incorporate a housing 50 forming an enclosure 54, needle shields 48 within the scope of the present disclosure need not fully encapsulate the needle tip to reduce the risk of needle sticks and blood exposure. As discussed above, a variety of safety clip configurations have been developed and may be developed that prevent needle sticks by closing and locking in position once the needle tip has been sufficiently retracted into the needle shield 48. FIGS. 7-11 illustrate schematically the use of a safety clip 64 as a protective device to shield the needle tip 42. The illustrated safety clip 64 is representative of the numerous protective devices that may be implemented to shield the needle tip 42. Additionally, as discussed above, although not specifically illustrated in FIGS. 1-5, safety clips may be incorporated into needle shields 48 having an enclosure, such as those discussed above.

Figure 7:
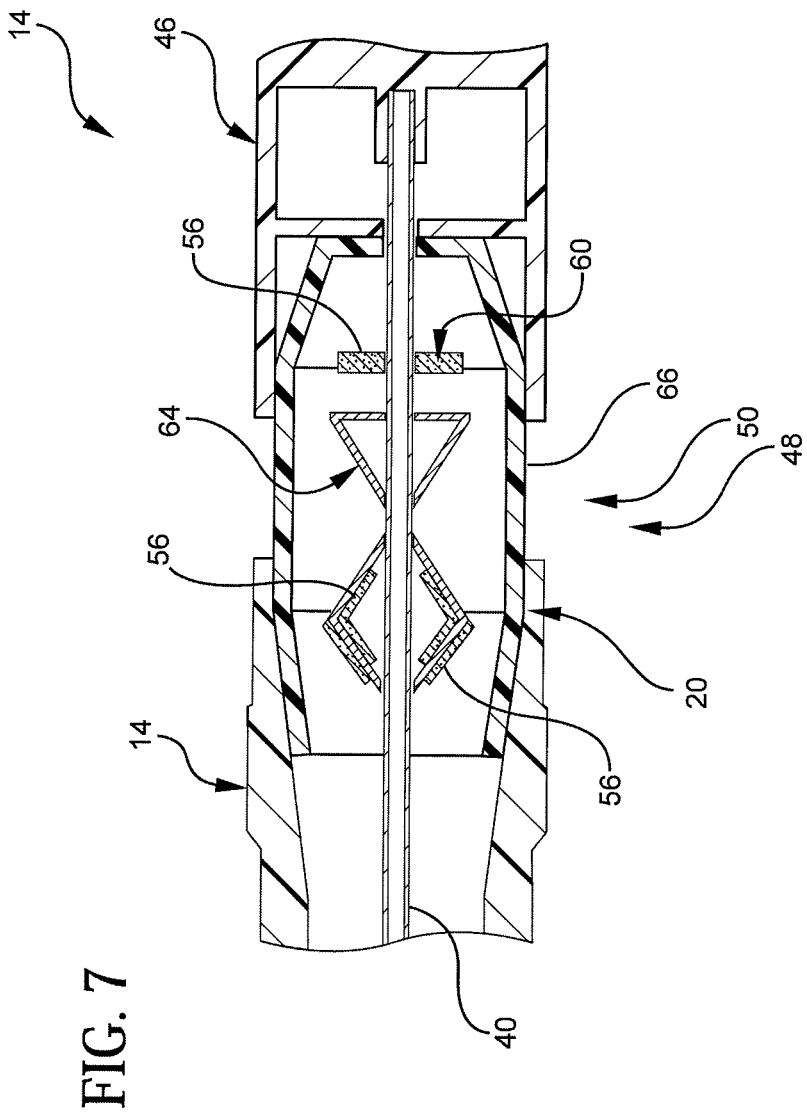
FIG. 7 is a cross-sectional view of an exemplary shield.

FIG. 7 illustrates a schematic cross-sectional view of a portion of an extravascular device 10, including a catheter assembly 14, a needle shield 48, and a needle 40. The needle shield 48 of FIG. 7 is configured as a needle collar 66 adapted to fit within the proximal end 20 of the catheter assembly 14. The needle collar 66 may be in any suitable configuration adapted to cooperate with the catheter assembly 14 and/or other vascular access devices 12. As used herein, the needle collar 66 is another example of a shield 48 incorporating a housing 50, which in this implementation does not form a full enclosure. FIG. 7 further illustrates that when the needle 40 is withdrawn from the catheter assembly 14, the safety clip 64 will close around the needle tip while the needle tip, and therefore a substantially portion of the blood associated with the needle, is still within the catheter assembly. Accordingly, it can be seen that in some implementations of the present disclosure, the housing 50 covers, or at least partially covers, a protective device, such as the safety clip 64, and is adapted to allow the protective device to shield the needle before the needle is completely withdrawn. The needle shield 48 may be provided in a variety of configurations that are adapted to cooperate with other vascular access devices to allow the safety clip 64 to close before the needle is completely withdrawn from the cooperating vascular access device. In some protective device configurations, the closing or engagement of the protective device as the needle is withdrawn may be a leading cause for blood splatter during withdrawal of the needle. Accordingly, providing a protective housing that cooperates with the adjoining vascular access device to allow the safety clip to close or otherwise shield the needle before the needle is withdrawn from the adjoining vascular access device may significantly decrease the amount of blood splatter and thereby reduce the risk of blood exposure.

FIG. 7 further illustrates that needle shields 48, regardless of the configuration particulars, may include blood stabilizing materials 56 to further limit the risk of blood exposure. As seen in FIG. 7, blood stabilizing materials 56 may be disposed on exterior and/or interior surfaces of the safety clip 64. Additionally or alternatively, blood stabilizing materials 56 may be disposed on or in association with one or more of the housing surfaces. Additionally or alternatively, blood stabilizing materials 56 may be incorporated as rings 60 surrounding the needle 40. As illustrated, in FIG. 7, the blood stabilizing materials 56 associated with the safety clip 64 are shown somewhat disproportionately to facilitate their visualization. As discussed above, the blood stabilizing materials 56 may be coagulants, absorbents, or other materials able to immobilize or stabilize blood. Additionally, the blood stabilizing materials 56 may be provided in liquid, solid, or gel form and may be coupled to the adjoining surfaces or applied as a coating.

While the blood stabilizing materials 56 have been discussed as being provided in liquid, solid, or gel form and being coupled or coated to different surfaces. FIG. 7 illustrates, by the uncoupled ring 60 that the blood stabilizing materials 56 may be provided in a variety of forms. As another illustrative example, the blood stabilizing materials 56 may be in powder, granular, or similar form and disposed in a porous membrane or container that allows blood to enter while preventing the exit of the blood stabilizing materials. Such a container of blood stabilizing materials may be disposed in a housing 50, and enclosure 54, or a collar 66, or may be coupled to one or more elements of the needle assembly 16.

With continuing reference to FIG. 7, the implementation of blood stabilizing materials 56 together with the housing configured to allow the safety clip to close before the needle is completely withdrawn may further reduce the risk of blood exposure. As discussed above, there may be relatively greater amount of blood splattered when the safety clip 64 closes over the tip of the needle. There may similarly be a larger amount of blood splattered as the needle tip exits a septum or other sealing member in the adjoining vascular access device. The proximate blood stabilizing materials 56 may further reduce the risk of blood exposure by absorbing or otherwise stabilizing such blood before the needle shield 48 is separated from the catheter assembly 14, or other adjoining vascular access device.

Figure 10:
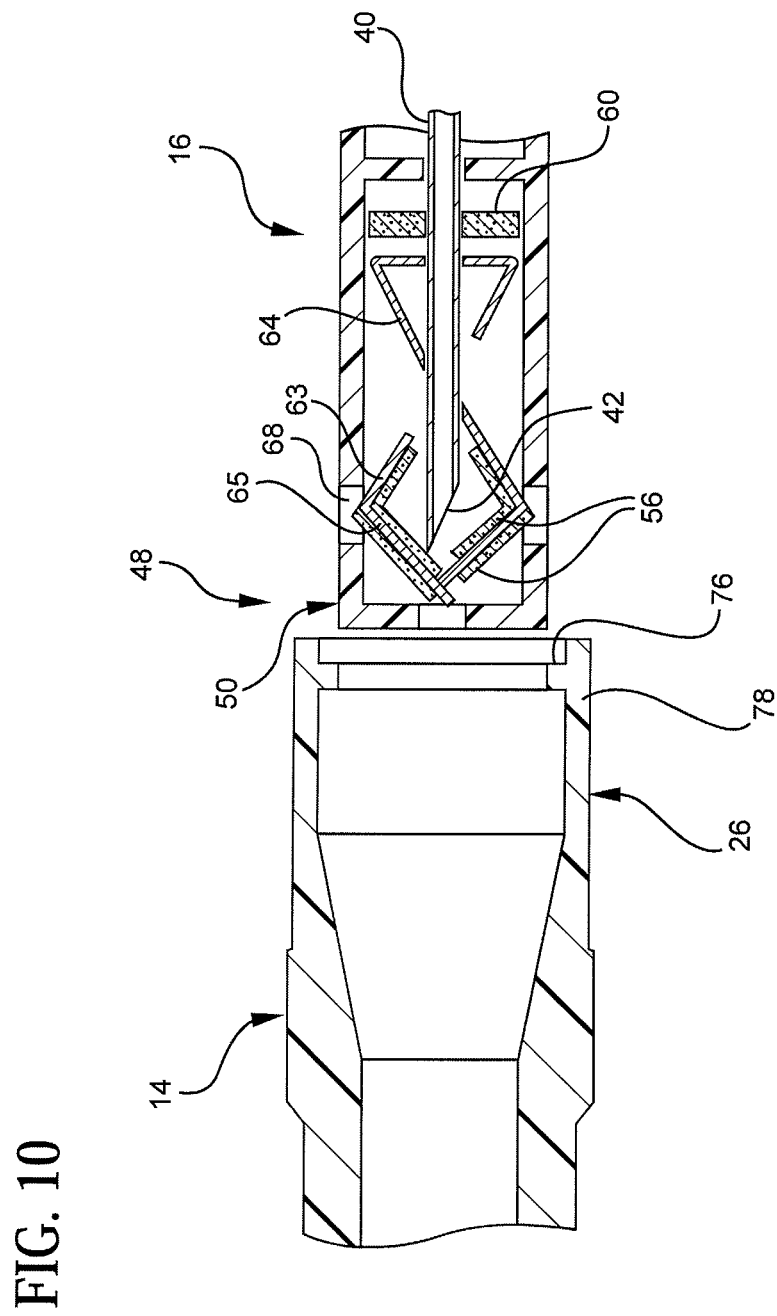
FIG. 10 is a cross-sectional view of the shield of FIG. 8 shown after the needle is withdrawn.

FIGS. 8-10 illustrate another exemplary shield configuration that may be used with or without blood stabilizing materials 56. However, as described in connection with FIG. 7, the use of blood stabilizing materials 56 may provide additional safety features for clinicians. As illustrated in FIGS. 8-10, the needle shield 48 provides a housing 50 that at least partially surrounds a protective device such as the safety clip 64. The housing 50 is illustrated in FIG. 8 as disposed within the catheter assembly 14, such as when the catheter assembly 14 and needle assembly 16 are provided from the manufacturer. FIG. 9 provides a perspective view of the needle assembly 16 separated from the catheter assembly 14 to better illustrate the relationships between the components of the needle assembly. As seen in FIGS. 8 and 9, the housing 50 may be provided as a substantial enclosure 54, or may be provided as a partial enclosure by opening one or both longitudinal ends of the housing.

FIGS. 8-10 illustrate that the shield 48 may be adapted to cooperate with the catheter assembly 14 to retain the shield 48 in the catheter assembly until the needle is sufficiently withdrawn that the safety clip 64 closes around the needle tip 42, as seen in FIG. 10. As shown in FIGS. 8 and 9, the elbows 65 of the arms 63 of the safety clip 64 extend through lateral ports 68 in the housing 50. Additionally, the catheter assembly 14 is provided with one or more retention fingers 76 extending radially inward from the outer wall 78 of the catheter hub 26. The size and configuration of the safety clip 64, the lateral ports 68, and the catheter hub 26 may be coordinated to retain the shield 48 within the catheter assembly 14 until the needle is sufficiently withdrawn. A variety of suitable configurations may be implemented. As illustrated, the safety clip 64 is biased to close over the needle tip 42, as seen most clearly in comparison of the clip in FIGS. 8 and 10 where the arms 63 are bent under tension in FIG. 8 and are relaxed in FIG. 10 after the clip 64 has closed over the needle tip. Once the needle tip 42 is withdrawn into the housing 50 sufficient to allow the safety clip 64 to engage and close over the needle tip, such as shown in FIG. 10, it can be seen that the elbows 65 are recessed into the housing 50 allowing the shield to be removed from the catheter assembly 14. The combination of elements illustrated in FIGS. 8-10 are illustrative of the various systems and combinations of elements that may be implemented to retain the needle assembly 16 and the catheter assembly 14 in a desired relationship until the needle is withdrawn to a predetermined and sufficient degree.

FIGS. 11 and 12 illustrate perspective views of needle shields 48 within the scope of the present disclosure. Similar to FIGS. 7-10, the needle shields 48 of FIGS. 11 and 12 include a housing 50 adapted to at least partially enclose a protective device, such as a safety clip 64, and to enclose the needle tip 42 when the needle tip is withdrawn. Similar to the illustrations of FIGS. 7-10, the housing 50 of FIGS. 11 and 12 provide an enclosure in which the needle tip is disposed when the safety clip 64 triggers to shield the needle tip 42. However, the housings 50 of FIGS. 11 and 12 are made of a flexible material compared to the materials of FIGS. 7-10 and forms what may be referred to as a flexible housing 70. It should be noted that the housings 50 of the present disclosure, including the housings illustrated in FIGS. 2-12, may be made of any suitable material, which may be a rigid material, a substantially rigid material, or a flexible material. The flexible material forming the flexible housing 70 may be selected from any suitable plastic or resin material that does not negatively react with blood or decompose on contact with blood.

The flexible housing 70 may be configured in a somewhat tubular formation as illustrated in FIGS. 11 and 12. The flexible housing 70 may allow the operator to form a tighter seal between the housing 70 and the adjacent vascular access device. The flexible housing 70 may be formed in a somewhat generic shape as illustrated in FIGS. 11 and 12 or may be shaped to more closely follow the contours of one or more vascular access devices to which the needle shield 48 may be coupled.

With reference to FIG. 11, the flexible housing 70 is illustrated as being substantially closed and providing a restricted passage 72 through the distal end 74 thereof. The restricted passage 72 may be sized to allow sliding engagement with the needle 40. In use, the flexible housing 70 of FIG. 11 may be disposed adjacent to or within a cooperating vascular access device. Additionally or alternatively, as with the other needle shields 48 described herein and the needle shields within the scope of the present disclosure and claims, the flexible housing 70 may be associated with a needle assembly 16 that is adapted to access a patient's vasculature directly without passing through another vascular access device, such as when the needle assembly 16 is used for injections. When used with a cooperating vascular access device, the flexible housing 70 of FIG. 11 with a restricted passage 72 may be adapted to fit within a sleeve formed by the adjoining vascular access device.

Regardless of whether used alone or in connection with another vascular access device, the needle shield 48 including the flexible housing 70 may allow the distal end 74 of the needle shield to be pressed closely against the adjoining surfaces. The closer fit of the needle shield to the adjoining surfaces may further limit the risk of blood exposure. Additionally, by configuring the flexible housing 70 to fit within a sleeve or other structure of an adjoining vascular access device, blood from the needle during the withdrawal process will be left within the adjoining vascular access device (e.g., catheter assembly, etc.) or will be brought into the enclosure formed by the flexible housing. Once the needle tip 42 is withdrawn into the flexible housing 70, the safety clip 64 may activate to shield the needle tip. As discussed above, activating the safety clip 64 within the enclosure may further reduce the risk of blood exposure by limiting the path of any splattered blood. Additionally, while not illustrated in FIGS. 11 and 12, needle shields 48 incorporating a flexible housing 70 may also incorporate blood stabilizing materials as described above.

As discussed above, FIG. 12 illustrates a flexible housing 70 at least partially encompassing a protective device, such as a safety clip 64, and adapted to enclose the needle tip when it is withdrawn. While the needle shield 48 of FIG. 12 includes a flexible housing 70 similar to the needle shield of FIG. 11, it is also similar to the needle shield 48 of FIG. 7. As discussed above in connection with FIG. 7, the needle shield 48 may be configured as a needle collar 66 adapted to fit within an adjoining vascular access device. The flexible housing 70 of FIG. 12 is configured as a needle collar 66 having a longitudinal opening 75. In some implementations, the longitudinal opening may be adapted to allow access into the housing by a medical device. As discussed above in connection with FIG. 7, a needle shield 48 incorporating a collar-like housing 66 may allow the protective device to engage and shield the needle tip before the needle is completely withdrawn from the adjacent vascular access device. By utilizing a flexible housing 70 to form the collar 66 of the housing 50, the needle shield 48 may be able to engage the adjoining vascular access device more fittingly to provide a better seal. Additionally or alternatively, the flexible housing 70 may allow the needle shield 48 to cooperate with a larger diversity of adjoining vascular access devices.

Similar to the discussion of the flexible housing in connection with FIG. 11, the flexible housing 70 forming a collar 66 in FIG. 12 may configure the needle assembly 16 for use in cooperation with other vascular access devices or as a standalone vascular access device, such as for injections. The flexible housing 70 forming a collar 66 may allow the needle shield 48 to form a better barrier with the patient's skin when serving as a stand-alone vascular access device. In some implementations, the longitudinal opening 75 may be provided by a beveled cut in the flexible housing to enable the distal end 74 of the flexible housing to better seal against the patient's skin or other adjoining surface.

The needle assemblies 16, the needle shields 48, and the safety clips 64 have been illustrated in FIGS. 11 and 12 as not including the blood stabilizing materials shown in several of the previous illustrations. However, as indicated above, blood stabilization materials in any of the forms and functionalities described herein may be incorporated in, coupled to, coated on, or otherwise associated with any one or more surfaces of a needle shield of any configuration. Accordingly, it should be understood that blood stabilizing materials may be provided in the configurations shown in FIGS. 11 and 12.

As discussed herein, when a hypodermic needle enters a subject's vasculature and is subsequently withdrawn there are various risks presented to those in the area. Needle sticks and exposure to the subject's blood are among the greatest risks. Exposure to blood is particularly problematic because once the subject's blood contacts another surface that surface is contaminated and must be discarded or sterilized. Additionally, blood exposure is a difficult risk to deal with because of the fluidic nature of blood. The fluidic nature allows it to move from one surface to another fairly easily, and to occasionally move through the air when splashed or splattered from a surface, such as when a sudden force is applied to the blood. As described thus far, methods of reducing blood exposure risks according to the present disclosure include one or more blood stabilizing means for limiting or restricting the ability of the blood to move freely. For example, the blood stabilizing materials described herein act to absorb the blood, coagulate the blood, or otherwise modify its fluidic nature into some more solid and less likely to splash, splatter, or otherwise move unexpectedly or unpredictably. Additionally, the blood stabilizing materials may be incorporated into a needle shield of any suitable configuration to further retain the blood stabilizing material and the blood in a desired location in the needle assembly. Still additionally, in some implementations, the housing provided to cooperate with the needle tip may be adapted to allow a safety clip or other protective needle tip shield device to engage before the needle is entirely withdrawn. Accordingly, any blood movement that may be caused or triggered by the engagement of the needle tip shield will be further contained and limited. These methods and systems may be combined in any suitable manner to provide improved apparatus for use with hypodermic needles to reduce the risk of blood exposure.

While limiting and restricting the possible paths of the blood may significantly reduce the risk of blood exposure, it may also be desirable to reduce the likelihood that the blood will be splattered or splashed to become airborne or otherwise leave the surface of the needle assembly. Hypodermic needles are designed to be inserted into patients and to be withdrawn therefrom, whether as a standalone vascular access device or in cooperation with other vascular access devices, such as catheters. Regardless of how the hypodermic needle is used and how it is inserted, the withdrawal of the needle often places various forces on the needle shaft. Most obviously, there are longitudinal forces applied as the needle is pulled rearward and friction, which may be minimal, resists the movement. However, despite great care by clinicians, lateral forces often are applied to the needle shaft as well. For example, the patient may move the body suddenly or the clinician may pull in a direction that is not perfectly rearward. In either situation or other situation in which a lateral force may be applied to either end of the needle, a bending moment is applied to the needle shaft unless the entire needle is subject to the same lateral forces. While such bending moments are not typically strong enough to break the needle, they are known to add energy to the system. When the needle tip is finally freed from the patient and/or adjoining vascular access device, that energy is often released through sudden, uncontrolled movement of the needle tip. As can be understood by the foregoing description, such movement may be at least partially responsible for causing some of the blood on the surface of the needle to become dislodged and even airborne.

Figure 13:
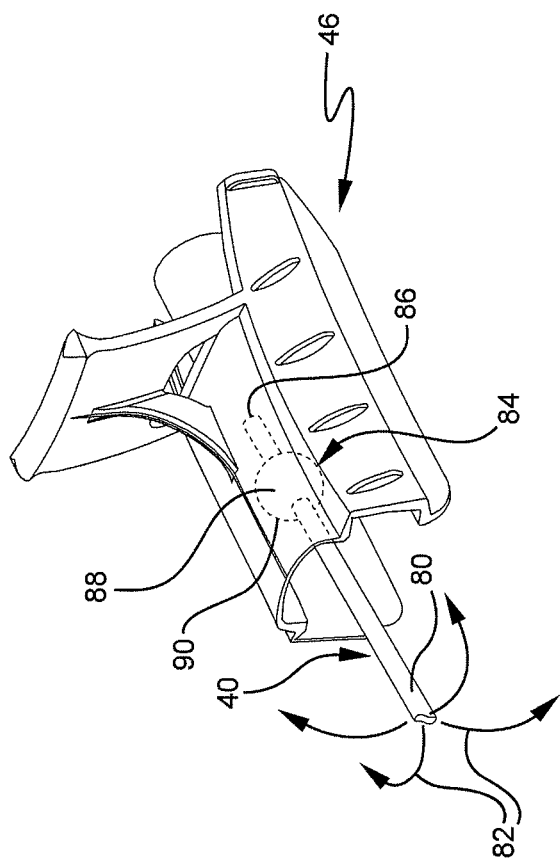
FIG. 13 is a perspective view illustrating the coupling of a needle shaft to a needle hub.

FIG. 13 schematically illustrates systems and methods for reducing the stored energy in a needle assembly from lateral forces. FIG. 13 illustrates a needle hub 46 and a needle 40 coupled thereto. The needle hub 46 may include a variety of structural and functional features, which may vary depending on the intended use of the needle assembly. For example, a needle assembly adapted to be used with a catheter assembly may include vents, flashback chambers, and other such features while a needle assembly adapted for use with a syringe as a single injection device may include other suitable features. As discussed above, the needle 40 includes a needle shaft 80 that may be subject to a variety of lateral forces, such as indicated by arrows 82. If the proximal end 86 of the needle shaft were fixedly coupled to the needle hub, one or more of these lateral forces 82 may apply a bending moment on the needle shaft 80 leading to energy build-up in the needle assembly. Accordingly, as illustrated in FIG. 13, the needle shaft 80 is provided with an articulation means 84 disposed within the needle hub 46. The articulation means 84 is adapted to allow the distal end of the needle shaft 80 to move in response to the lateral forces 82 while retaining the proximal end 86 in the proper position within the needle hub 46.

The articulation means 84 may be provided by any suitable combination of structural features. As illustrated in FIG. 13, the articulation means 84 is provided by a simple ball-and-socket joint, including articulation ball 88 and articulation socket 90. The articulation socket 90 may be configured to retain the articulation ball 88 in a fixed longitudinal position while allowing the needle shaft some range of lateral motion. In some implementations, it may be desirable to limit axial rotation of the needle shaft, such as when the beveled needle has a preferred orientation relative to the patient's skin. Accordingly, the articulation means 84 may include one or more features to limit such rotation, such as one or more wings on the articulation ball 88 to coordination with one or more grooves in the articulation socket. Additionally or alternatively, the articulation means may be provided by coordination elements that are not spherical, such that the corners of the coordinating elements function to limit rotation.

As can be seen in FIG. 13, the articulation means 84 provided by the articulation ball 88 and the articulation socket 90 may be adapted to provide a pivot point about which the needle shaft can pivot. When the articulation means 84 is disposed sufficiently close to the proximal end 86 of the needle shaft, movement or pivoting about the articulation means will not sufficiently displace the proximal end of the needle shaft. Additionally or alternatively, the articulation means may be provided by elements that allow for a pivot point in the needle shaft and for actual lateral movement of the needle shaft. For example, in the context of an articulation means provided by a ball-and-socket joint, the articulation ball 88 may be configured somewhat smaller than the articulation socket 90 to allow the entire needle shaft to shift as necessary to relieve stress and energy that may build in the needle system during use.

The articulation means 84 may be provided by any suitable combination of elements that associates and couples the needle shaft 80 to the needle hub 46 while allowing movement of one or more ends of the needle shaft 80. A needle assembly 46 incorporating an articulation means 84 may allow the configuration of the needle assembly to vary slightly during use to reduce and/or eliminate energy build-up that may occur due to application of one or more lateral forces on the needle.

It is believed that the disclosure set forth above encompasses multiple distinct methods and/or apparatus with independent utility. While each of these methods and apparatus has been disclosed in its preferred form, the specific embodiments thereof as disclosed and illustrated herein are not to be considered in a limiting sense as numerous variations are possible. The subject matter of the disclosures includes all novel and non-obvious combinations and subcombinations of the various elements, features, functions and/or properties disclosed herein. The principles of the present disclosure may be embodied in other specific forms without departing from its structures, methods, or other essential characteristics as broadly described herein. The described embodiments are to be considered in all respects only as illustrative, and not restrictive. The scope of the disclosure is, therefore, not limited by the foregoing description or the following claims, and all changes that come within the meaning and range of equivalency of the foregoing description and/or the following claims are to be embraced within its scope. Similarly, where the description and/or the claims recite "a" or "a first" element or the equivalent thereof, such description should be understood to include incorporation of one or more such elements, neither requiring nor excluding two or more such elements.

It is believed that the following claims are directed to certain combinations and subcombinations that correspond to disclosed examples and that are believed to be novel and non-obvious. Other combinations and subcombinations of features, functions, elements and/or properties may be claimed through amendment of the present claims or presentation of new claims in this or a related application. Such amended or new claims, whether they are directed to a different combination or directed to the same combination, whether different, broader, narrower or equal in scope to the original claims, are also regarded as included within the subject matter of the present disclosure.

The invention claimed is:

1. An apparatus for preventing blood contamination upon withdrawal of a hypodermic needle comprising:
   a needle having a shaft, a distal tip, a proximal portion, and a proximal end, the proximal portion of the needle being contained within a needle hub, the proximal portion including a lateral force dampening member positioned on the needle distally from the proximal end, the lateral force dampening member forming a pivot point for lateral movement of the distal tip and proximal end such that a lateral force applied to the distal tip in a first direction will cause the proximal end to move laterally in an opposite direction;
   a shield configured to at least partially entrap the needle tip upon withdrawal of the needle; and
   a blood stabilizing material disposed on a surface of the shield.

2. An apparatus as defined in claim 1 wherein the blood stabilizing material comprises at least one of an absorbent material and a coagulant.

3. An apparatus as defined in claim 1 wherein the shield comprises a safety clip and at least a portion of the blood stabilizing material is disposed on a surface of the safety clip.

4. An apparatus as defined in claim 1 wherein the blood stabilizing material is a solid.

5. An apparatus as defined in claim 1 wherein the blood stabilizing material is a liquid.

6. An apparatus as defined in claim 1, wherein the shield includes a protective device for shielding the needle tip upon withdrawal, and wherein the blood stabilizing material is disposed on at least one surface of the protective device.

7. An apparatus as defined in claim 1, wherein the shield includes a protective device adapted to shield the needle tip upon withdrawal and a housing adapted to at least partially enclose the protective device, and wherein the housing is adapted to allow the protective device to shield the needle tip before the needle is completely withdrawn.

8. An apparatus as defined in claim 7, wherein the blood stabilizing material is associated with the protective device.

9. An apparatus as defined in claim 7 wherein the housing is substantially rigid.

10. An apparatus for preventing blood contamination upon withdrawal of a hypodermic needle comprising:
   a needle hub; and
   a needle having a shaft, a distal tip, a proximal portion, and a proximal end, the proximal portion of the needle being contained within the needle hub, the proximal portion including a lateral force dampening member positioned on the needle distally from the proximal end, the lateral force dampening member forming a pivot point for lateral movement of the distal tip and proximal end such that a lateral force applied to the distal tip in a first direction will cause the proximal end to move laterally in an opposite direction.

11. The apparatus of claim 10, wherein the lateral force dampening member is a ball, and the needle hub further comprises a socket in which the ball is positioned.

12. The apparatus of claim 11, wherein the socket limits axial rotation of the needle.

13. The apparatus of claim 11, wherein the socket limits longitudinal motion of the needle.

14. The apparatus of claim 10, wherein the lateral force dampening member limits axial rotation of the needle.

15. The apparatus of claim 11, wherein the ball includes one or more wings which interact with one or more grooves in the needle hub to limit axial rotation of the needle.

16. The apparatus of claim 1, wherein the lateral force dampening member is a ball, and the needle hub further comprises a socket in which the ball is positioned.

17. The apparatus of claim 1, wherein the lateral force dampening member limits one or more of axial or longitudinal motion of the needle.

18. The apparatus of claim 16, wherein the ball includes one or more wings which interact with one or more grooves in the needle hub to limit axial rotation of the needle.

19. An intravenous device comprising:
   a catheter adapter;
   a needle hub configured to interlock with the catheter adapter;
   a needle having a proximal portion that is contained within the needle hub and a distal portion that extends through the catheter adapter, the proximal portion including a lateral force dampening member positioned on the needle distally from a proximal end, the lateral force dampening member forming a pivot point for lateral movement of the distal tip and proximal end such that a lateral force applied to the distal tip in a first direction will cause the proximal end to move laterally in an opposite direction.

20. The intravenous device of claim 19, wherein the needle hub includes a socket and the lateral force dampening member comprises a ball that sits within the socket thereby enabling the ball to rotate within the socket to laterally displace the proximal end of the needle when a lateral force is applied to the distal tip.

* * * * *